(12) United States Patent
Schultz

(10) Patent No.: US 8,575,194 B1
(45) Date of Patent: Nov. 5, 2013

(54) TREATMENT METHODS OF COGNITIVE, EMOTIONAL AND MENTAL AILMENTS AND DISORDERS

(76) Inventor: Jack William Schultz, Alpharetta, GA (US)

(*) Notice: Subject to any disclaimer, the term of this patent is extended or adjusted under 35 U.S.C. 154(b) by 227 days.

(21) Appl. No.: 11/213,018

(22) Filed: Aug. 26, 2005

Related U.S. Application Data

(60) Provisional application No. 60/606,003, filed on Aug. 31, 2004.

(51) Int. Cl.
*A61K 31/47* (2006.01)

(52) U.S. Cl.
USPC .......................................................... 514/311

(58) Field of Classification Search
USPC .......................................................... 514/311
See application file for complete search history.

(56) References Cited

U.S. PATENT DOCUMENTS

| | | | |
|---|---|---|---|
| 5,391,555 | A | 2/1995 | Marshall et al. |
| 5,629,337 | A | 5/1997 | Gray |
| 6,248,308 | B1 | 6/2001 | Rubin |
| 6,423,721 | B1 | 7/2002 | Harris et al. |
| 6,440,994 | B1 | 8/2002 | Sanders, Jr. |
| 6,576,636 | B2 | 6/2003 | Webb et al. |
| 6,696,466 | B1 | 2/2004 | Dunaway |
| 6,762,193 | B1 | 7/2004 | Sanders, Jr. |
| 2002/0137785 | A1 | 9/2002 | Kindness et al. |

OTHER PUBLICATIONS

Craig TJ, McCann JL, Gurevich F, and Davies MJ, "The correlation between allergic rhinitis and sleep disturbance," Journal of Allergy and Clinical Immunology, Nov. 2004, 114(5 Suppl), S139-S145.*
Lieberman HR, "The effects of ginseng, ephedrine, and caffeine on cognitive performance, mood and energy," Nutrition Reviews, Apr. 2001, 59(4), 91-102.*
Philip G, Malmstrom K, Hampel FC, Weinstein SF, LaForce CF, Ratner PH, Malice MP, and Reiss TF, "Montelukast for treating seasonal allergic rhinitis: a randomized, double-blind, placebo-controlled trial performed in the spring," Clinical and Experimental Allergy, Jul. 2002, 32(7), 1020-1028.*
American Heritage Dictionary of the English Language, Boston, MA, Houghton Mifflin, 2007.*
Drugs.com, Montelukast, accessed on Apr. 11, 2009, http://www.drugs.com/ppa/montelukast-sodium.html.*
Drugs.com, Zafirlukast, accessed on Apr. 13, 2009, http://www.drugs.com/mtm/zafirlukast.html.*
Altman LC, Munk Z, Seltzer J, Noonan N, Shingo S, Zhang J, and Reiss TF, "A placebo-controlled, dose-ranging study of montelukast, a cysteinyl leukotriene-receptor antagonist. Montelukast Asthma Study Group," Journal of Allergy and Clinical Immunology, Jul. 1998, 102(1), 50-56.*
Blaiss MS, "Cognitive, social, and economic costs of allergic rhinitis," Allergy and Asthma Proceedings, Jan.-Feb. 2000, 21(1), 7-13.*

* cited by examiner

*Primary Examiner* — Paul Zarek
(74) *Attorney, Agent, or Firm* — Taylor English Duma, LLP

(57) ABSTRACT

Methods for the treatment of cognitive, emotional and mental ailments using therapeutically effective amounts of compositions including leukotriene receptor antagonists, leukotriene synthesis inhibitors or leukotriene modifiers, zafirlukasts, montelukasts, other members of the family -lukasts, zileutons.

13 Claims, No Drawings

TREATMENT METHODS OF COGNITIVE, EMOTIONAL AND MENTAL AILMENTS AND DISORDERS

Priority based on U.S. Provisional Patent Application Ser. No. 60/606,003, filed Aug. 31, 2004, and entitled "Treatment Methods of Cognitive Emotional and Mental Ailments and Disorders" is claimed.

BACKGROUND

I. Field of the Invention

The present invention relates generally to the field pharmaceuticals and treatment of ailments, and more particularly to a method for treatment of cognitive, emotional and mental ailments.

II. Description of the Related Art

At an increasing rate, people are suffering from a series of mental, emotional and cognitive disorders and ailments from a variety of sources. In particular, with the inevitable aging of the Baby Boomer generation, a larger number of people are experiencing these disorders and ailments. This particular generation is interested in keeping mental, emotional and cognitive focus with fewer solutions to these ailments and disorders. However, there is increasing discontent as to remedies available to address these ailments and disorders.

SUMMARY

In general, the invention features methods for the treatment of cognitive, emotional and mental ailments using therapeutically effective amounts of compositions including leukotriene receptor antagonists, leukotriene synthesis inhibitors or leukotriene modifiers, zafirlukasts, montelukasts, other members of the family -lukasts, zileutons.

In general, the invention features a method, including administering to a patient suffering from a family of mental, emotional and cognitive ailments a therapeutically effective amount of a composition affecting the ailment for a specified period of time for relief of the ailments.

In one implementation, the composition is a leukotriene receptor antagonist.

In another implementation, the composition is a leukotriene synthesis inhibitor.

In another implementation, the composition is a leukotriene modifier.

In another implementation, the composition is a montelukast.

In another implementation, the composition is a zafirlukast.

In another implementation, the composition is a zileuton.

In yet another implementation, the composition is a member of the family -lukast.

In still another implementation, the composition is administered at an initial dosage of about 20-30 mg.

In another implementation, additional dosages are administered at periodic intervals.

In another implementation, the additional dosage is about 5 mg.

In another implementation, the additional dosage is about 10 mg.

In another implementation, the additional dosage is about 20 mg.

In another implementation, the periodic interval is about every 2 hours.

In another implementation, the periodic interval is about every 4 hours.

In another implementation, the maximum daily dosage is about 40 mg.

In another implementation, the maximum daily dosage is about 80 mg.

In another implementation, the ailments result from mild permanent cognitive and short term memory loss.

In another implementation, the ailments are caused by prolonged exposure to levels of mold and fungi.

In another implementation, the mold is Stachybotrus.

In another implementation, the ailments can be related to prolonged allergies.

One advantage of the invention is that the compositions used in the treatment methods have little to no significant side effects.

Another advantage of the invention is that prolonged marked improvement of several cognitive, mental and emotional ailments is realized.

Other objects, advantages and capabilities of the invention will become apparent from the following description taken in conjunction with the accompanying drawings showing the preferred embodiment of the invention.

DETAILED DESCRIPTION

In general, the methods described herein are implemented for the treatment of treatment of ailments such as cognitive, emotional and mental disorders. In a specific embodiment, pharmaceutically acceptable doses of leukotriene receptor antagonists, leukotriene synthesis inhibitors or leukotriene modifiers are used to reduce or eliminate several classes of cognitive, emotional and mental disorders. It is understood that these classes spread across a wide spectrum of disorders including, but not limited to memory loss, which can include simple short term or long term memory loss, senility, Alzheimer's, vascular dementia and other types of memory loss and dementia; apathy; depression, fatigue; cognitive losses; loss of focus; loss of libido; loss of the ability to multi-task; loss of sense of humor; repetitive daydreaming; attention deficit disorders and the like.

The leukotriene receptor antagonists, leukotriene synthesis inhibitors or leukotriene modifiers can include a large class of compositions including but not limited to zafirlukasts, montelukasts, other members of the family -lukasts, zileutons.

In a specific embodiment, the method can be used for the treatment of loss of cognitive, mental and emotional ability due to permanent cognitive and mental damage.

Such damage can be caused by several reasons including the prolonged exposure to toxic levels of mold that can include Stachybotrus molds and other fungi. Such exposure to the molds can be accompanied by strong allergic reactions that can typically cease when the person leaves the physical location of the molds. However, it has been determined that the prolonged exposure to the molds can cause mild permanent cognitive and short term memory loss and other conditions that can result in the cognitive, mental and emotional ailments as described above and further in the example below.

By obtaining treatment of certain classes of compositions, those experiencing the ailments from mild permanent cognitive and short term memory loss and other cognitive, mental and emotional conditions can obtain significant relief. In one implementation, the person suffering from the ailments can take an increased dosage of the compositions, typically 2-3 times the dosage of the same medication used in the treatment of allergies, as an initial dosage at the beginning of the day and can experience almost immediate relief from the ailments. By taking an additional dosage periodically during the day, the patient can experience relief from the ailments all day. In a specific implementation, the initial increased dosage can be 20-30 milligrams of a montelukast sodium compound such as Singulair®, in which marked improvement is noticed within 30-45 minutes. Additional smaller dosages, such as about 10 mg can be taken at four hour intervals to experience prolonged relief.

There can be several mechanisms which can cause the cognitive, mental and emotional ailments resulting from mild permanent cognitive and short term memory loss and other cognitive, mental and emotional conditions. In additional, it is understood that there are several mechanisms that can cause the relief upon administration of the composition such as, but not limited to the mechanisms associated with leukotriene receptor antagonists, leukotriene synthesis inhibitors or leukotriene modifiers, as well as simple relief from chronic inflammation that can result in neurological effects.

EXAMPLE

A case study of a patient having a long history of allergies was performed. During his teenage years, the patient had allergies, but enjoyed forty five years of freedom from allergies. Late in 1995, the patient had recurring allergies and additional allergies previously not present. The patient suffered chronic sinusitis and sought the services of an Eye Nose Throat group. Under typical treatment, the conditions did not improve and in 1997 the patient had sinus surgery and rhinoplasty. Shortly thereafter, the symptoms returned and continued through 2003. The patient then began experiencing cognitive, mental and emotional ailments that appeared to have no connection to his chronic allergies. These ailments included short term or long term memory loss, dementia, apathy, depression, fatigue and chronic fatigue, cognitive losses, loss of focus, "foggy days", loss of libido, loss of the ability to multi-task, loss of sense of humor, repetitive daydreaming, loss of the sense of time, and disorientation.

Concurrently in 1999, the patient found that his business location had toxic levels of mold that had been growing in the workplace from 1995 forward. Stachybotrus and other fungi had been present during the outset of the allergies in 1995. Through blood tests the patient was found to have a "hole" in his immune system and as a result had a high sensitivity to these and other molds. In general, the patient was ordered in 2000 not to return to the workplace until it was cleaned of dangerous high levels of mold. The recommended course of action of leaving the source of the mold typically results in patients marked improvement in the allergic condition. However, the patient discovered that the cognitive, mental and emotional ailments persisted. His general health deteriorated to a point where he could wake up and not be aware of his own name until after several hours of being awake. For a period of five months the patient could wake up, remember his name after a few hours and if prompted by a reminder from a family member, could perform daily tasks. Even with reminders, the patient experienced apathy that resulted in the tasks being ignored.

The patient was able to seek the help of mold experts in 2001 who recommended staying away from mold, but diagnosed the patient with mild permanent cognitive and short term memory loss that were apparently the devastating results of being exposed to the mold. The patient was used to being a business man who had the great ability to multitask and run several successful businesses. The patient now found himself struggling to meet the basic needs of everyday living. With great effort, the patient could focus to complete simple tasks.

The patient was still experiencing allergies, so in an unrelated trip to an allergy physician, the patient was prescribed the medication Singulair®. The patient discovered that when he took the medication, he experienced cognitive improvement. A typical dosage of the Singulair® is about 10 mg. On a trial basis, the patient took approximately 2-3 times the dosage or about 20-30 mg and found marked cognitive, mental and emotional improvement. The patient also experienced a marked decrease in apathy and an increase in sense of humor. Upon waking, the patient takes the higher dosage of Singulair® and experiences relief from the diagnosed mild permanent cognitive and short term memory loss in about 30-45 minutes. Furthermore, taking an additional 10 mg dose every four hours continues the relief from the diagnosed mild permanent cognitive and short term memory loss, which includes the other symptoms the patient was experiencing. When the patient ceases the dosage, the symptoms typically return in a 24 hour period.

In one embodiment, as described in the example, montelukast sodium can be implemented to treat the ailments and disorders as described. A 10 mg tablet can be taken orally upon awakening. Typically, in about 45 minutes to one hour, a patient can experience relief from the ailments and disorder and begin to have better mental focus on daily routines. In a typical implementation, the patient can take another 10 mg dose in about two hours after the initial dose. Booster dosages of about 5 mg, typically in a chewable tablet, can be taken to have heightened focus throughout the day. Similar booster dosages can be taken at 3-4 hour intervals throughout the day. In another implementation, an additional 10 mg dose can be taken after the second 5 mg dose if such advantageous effects wear off. Additional 10 mg doses can be taken to achieve higher effects of focus. In another implementation, booster dosages of 5 mg can be taken at intervals of about every 2 hours in order to achieve very high levels of focus. It has been determined that such mega-dosing can result in very talkative mental states and highly sensitive mental alertness. In the example discussed above, a maximum dose of 40 mg in one day has been taken. The Singulair® product typically recommends 10 mg per day.

In another embodiment, a zafirlukast product such as Accolate® and Vanticon® can be implemented. In one implementation, a 20 mg oral dose can be taken upon awakening followed by a 10 mg dose after 2 hours and a 10 mg repeated dose in 4 hours and a final dose of 20 mg another 4 hours later. Accolate® provides heightened focus but results in a less "wired" disposition. The highest dosage taken by the patient in the example above has been 80 mg in a daily dosage. The Accolate® recommended dosage is 20 mg in the morning and evening.

In other embodiments, other leukotriene modifiers can be implemented including but not limited to Zyflow® (zileuton), Onon® (pranlukast), Azlaire® (pranlukast) and Xolair (omalizumab).

The methods of administering the compositions described herein can also be implemented to treat other disorders including but not limited to restless leg disorder and the like.

The foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A method, comprising administering to a patient suffering from cognitive short term memory loss, a therapeutically effective amount of a composition comprising a member of the family -lukast, wherein the composition reverses said cognitive short term memory loss for a specified period of time for relief, said method further comprising:

administering orally a 10 mg first dose of montelukast sodium upon awakening;

administering a 10 mg second dose of montelukast sodium about two hours after said first dose;

administering a 5 mg third dose of montelukast sodium about three to four hours after said second dose;

administering a 5 mg fourth dose of montelukast sodium about three to four hours after said third dose;

optionally administering a 10 mg fifth dose of montelukast sodium about three to four hours after said fourth dose.

2. A method for treating memory loss in a human comprising the steps of:

administering to a patient with memory loss a first dosage of a therapeutically effective amount of a composition comprising montelukast sodium, wherein the initial dose of the composition comprises at least 10 mg of montelukast sodium, wherein the memory loss is not the result of ongoing allergies, and administering a second dosage of the composition, wherein the second dose of the composition comprises at least 5 mg of montelukast sodium, wherein the second dosage is administered between 2-4 hours after the first dosage.

3. The method of claim 2, comprising the administration of a third dose of the composition comprising montelukast sodium.

4. The method of claim 3, wherein the third dose is greater than 5 mg.

5. The method of claim 3, wherein the third dosage is administered between about 2-4 hours after the second dosage.

6. The method of claim 3, additionally comprising the administration a fourth dose of the composition comprising montelukast sodium, wherein the additional dose of montelukast sodium is 5 mg.

7. The method of claim 6, wherein the fourth dosage is administered between about 2-4 hours after the second dosage.

8. A method for improving cognitive function in a human comprising the steps of:

administering to a patient with cognitive impairment a first dosage of a therapeutically effective amount of a composition comprising montelukast sodium, wherein the initial dose of the composition comprises at least 10 mg of montelukast sodium, wherein the cognitive impairment is not the result of ongoing allergies, and administering a second dosage of the composition, wherein the second dose of the composition comprises at least 5 mg of montelukast sodium, wherein the second dosage is administered between 2-4 hours after the first dosage.

9. The method of claim 8, comprising the administration of a third dose of the composition comprising montelukast sodium.

10. The method of claim 9, wherein the third dosage is administered between about 2-4 hours after the second dosage.

11. The method of claim 9, wherein the third dose is greater than 5 mg.

12. The method of claim 9, additionally comprising the administration a fourth dose of the composition comprising montelukast sodium, wherein the additional dose of montelukast sodium is 5 mg.

13. The method of claim 12, wherein the fourth dosage is administered between about 2-4 hours after the third dosage.

* * * * *